United States Patent [19]

Bellotti et al.

[11] Patent Number: 4,596,571
[45] Date of Patent: Jun. 24, 1986

[54] SHROUD FOR PROTECTING AND STRENGTHENING A CONNECTION SITE

[75] Inventors: Marc Bellotti, Winnetka, Ill.; Randy K. Murphey, Kenosha, Wis.

[73] Assignee: Baxter Travenol Laboratories, Inc., Deerfield, Ill.

[21] Appl. No.: 734,363

[22] Filed: May 14, 1985

[51] Int. Cl.$^4$ .......................... A61B 19/00; A61M 5/32
[52] U.S. Cl. .................................................. 604/411
[58] Field of Search .................. 604/29, 283, 411, 905, 604/165, 93; 285/260, 373, 419; 128/334 C

[56] References Cited

U.S. PATENT DOCUMENTS

| | | | |
|---|---|---|---|
| 3,628,813 | 12/1971 | Lee, Jr. et al. ................. | 128/334 C |
| 4,402,691 | 9/1983 | Rosenthal et al. ................. | 604/905 |
| 4,405,312 | 9/1983 | Gross et al. ...................... | 604/905 |
| 4,432,759 | 2/1984 | Gross et al. ...................... | 604/905 |
| 4,473,369 | 9/1984 | Lueders et al. ..................... | 604/905 |

Primary Examiner—C. Fred Rosenbaum
Assistant Examiner—Michelle N. Lester
Attorney, Agent, or Firm—Paul C. Flattery; Daniel D. Ryan

[57] ABSTRACT

A protective shroud for a connection site also strengthens the connection site by restraining movement of the connection site in a manner which would cause its separation. One end of the protective shroud is buttressed to resist yielding in response to forces acting upon the connection site. When an oversized connection site is inserted into the shroud, the shroud provides a camming action which compresses the connection site to a length which securely nests within the shroud.

3 Claims, 9 Drawing Figures

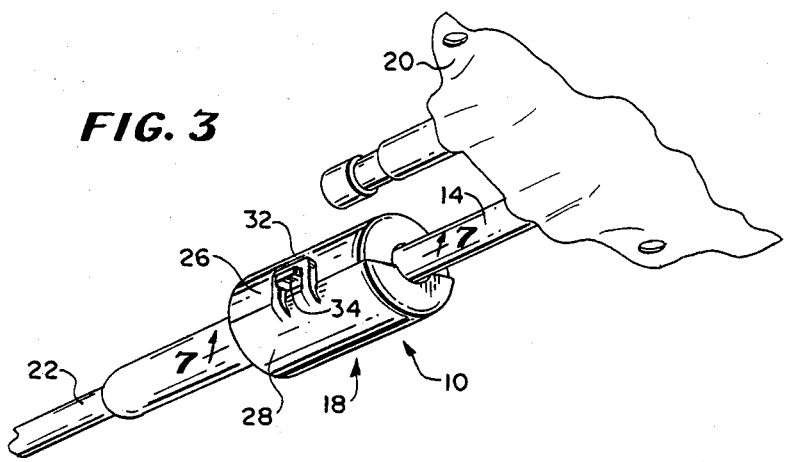
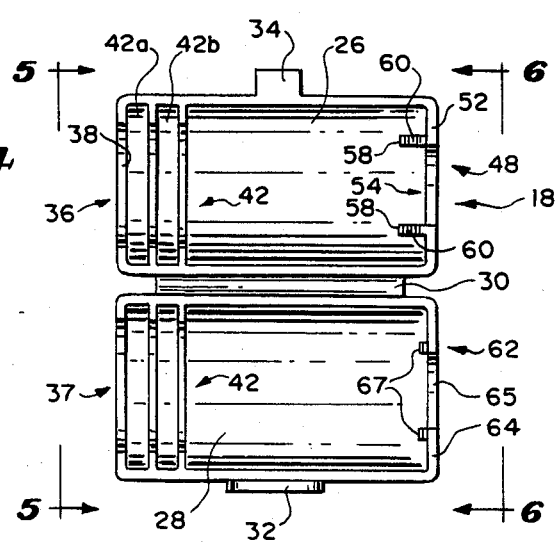
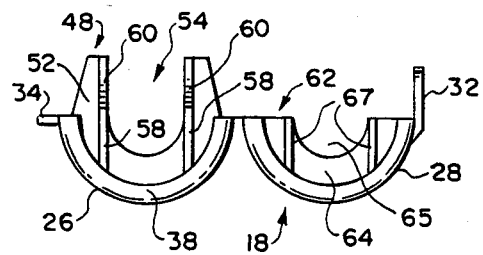
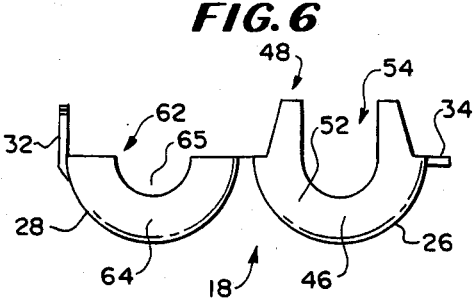

4,596,571

SHROUD FOR PROTECTING AND STRENGTHENING A CONNECTION SITE

FIELD OF THE INVENTION

The invention relates to devices intended to surround and protect the connection site between fluid conduits, particularly in the medical field.

BACKGROUND OF THE INVENTION

It is known in the medical field that closures, or shrouds, can be used to protect a connection site from touch contamination.

For example, in Gajewski et al U.S. Pat. No. 3,456,965, a connection site protector for fluid conduits is disclosed. The protector comprises two semicircular shells which are hinged together to peripherally surround two fluid conduits at their point of connection.

In Dennehey et al U.S. Pat. No. 4,340,052, another connection site protector is disclosed. This protector, like Gajewski et al, comprises two semicircular shells which are hinged together. A sterilizing agent is housed within the shells in contact with the connection site.

Also, in Rogers U.S. Pat. No. 4,354,490, yet another connection site protector connector for fluid conduits is shown. In one embodiment, the site protector is generally cylindrical. The fluid conduits are slid through opposite ends of the protector to form the connection site. As in Dennehey et al, a sterilizing agent is housed within the confines of the site protector.

SUMMARY OF THE INVENTION

The invention provides an improved protective shroud for a connection site.

The protective shroud includes mating first and second housing shells which, when brought together, peripherally surround the connection site and protect the connection site from touch contamination. Both ends of the connection site are securely nested within the shroud. The shroud not only protects the connection site against touch contamination, but it also strengthens the connection site. The connection site is thus able to withstand forces which, in the absence of the shroud, would break the connection site apart.

In accordance with the invention, one end of the connection site is nested within the shroud against a restraining wall located on one of the housing shells. The restraining wall has an associated camming surface. As one end of the connection site is pressed into the confines of the shroud and into contact with the restraining wall, the connection site is compressed by the camming surface to a length in which the connection site securely nests within the shroud.

In a preferred embodiment, a second wall is located on the other one of the housing shells. When the housing shells are brought together, the second wall overlaps and presses against the exterior of the restraining wall. The overlapping wall buttresses and strengthens the restraining wall to withstand the forces which are encountered in keeping the connection site secure.

The invention assures that the connection site is uniformly lodged within the shroud in a secure manner. Also, the invention provides a shroud which can readily accept connection sites of differing sizes.

Other features and advantages of the invention will be pointed out in, or will be apparent from, the specification and claims, as will obvious modification of the embodiments shown in the drawings.

BRIEF DESCRIPTION OF THE DRAWINGS

FIG. 3 is a perspective view of the protective shroud as it surrounds and protects the connection site shown in FIG. 2;

FIG. 4 is a top view showing the interior of the protective shroud shown in FIG. 1;

FIG. 5 is an end view of the protective shroud taken generally along line 5—5 in FIG. 4;

FIG. 6 is an end view of the protective shroud taken generally along line 6—6 in FIG. 4;

Before explaining the embodiments of the invention in detail, it is to be understood that invention is not limited in this application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed is for the purpose of the description and should not be regarded as limiting.

DESCRIPTION OF THE PREFERRED EMBODIMENTS

Figure 1:
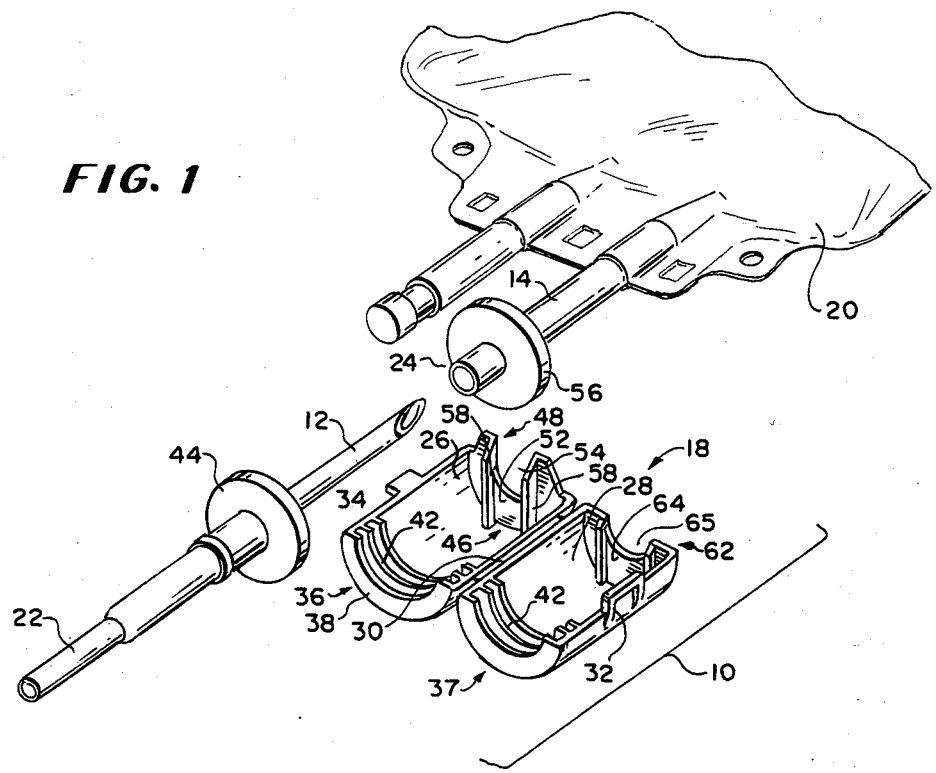
FIG. 1 is a perspective view of a connection system which includes two mating connectors and a protective shroud which incorporates the features of the invention.

A connection system 10 is shown in FIG. 1. The system 10 includes first and second connectors 12 and 14 which, when coupled together, form a connection site 16 (see FIG. 2). The system 10 also includes a protective shroud 18 for the connection site 16.

The connection system 10 which will be described can be used in a diverse number of environments. In FIG. 1, the system 10 is used to establish fluid communication between a solution container 20 and an administration set 22. As such, the illustrated system 10 can be used in the practice of continuous ambulatory peritoneal dialysis (CAPD) or in the administration of parenteral fluids in general.

In the illustrated use, the first connector 12 takes the form of a spike member which is attached to the end of the administration set 22. The second connector 14 takes the form of a tubular outlet port on the solution container 20. A membrane 24 occupies the port 14 to normally prevent fluid flow from the container 20.

Figure 2:
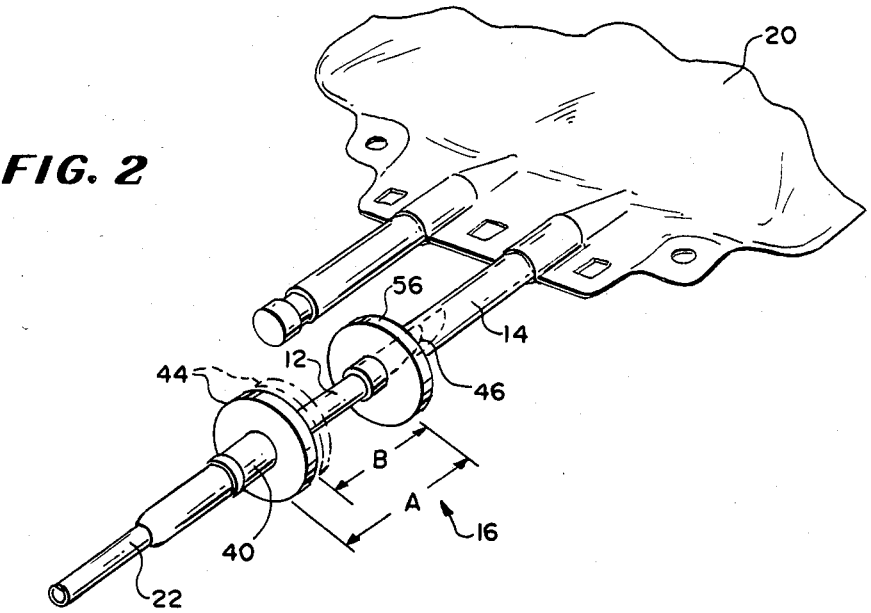
FIG. 2 is a perspective view of a connection site formed between the two connectors shown in FIG. 1.

As shown in FIG. 2, the spike member 12 can be slidably inserted into the port 14 by the application of force, either manually or by use of a connection assist device. During insertion, the spike member 12 pierces the membrane 24. This opens fluid communication between the administration set 22 and the contents of the container 20. The connection site 16 is thereby formed.

As shown in FIG. 3, the shroud 18 is attachable to the connection site 16. Once attached, the shroud 18 protects the site 16 against touch contamination. In accordance with the invention, the shroud 18 also serves to strengthen the connection site 16 to prevent accidental separation of the spike member 12 from the port 14.

Reference is now made principally to FIGS. 1 and 4 to 6. There, the shroud 18 is shown to comprise mating first and second housing shells 26 and 28. The shells 26 and 28 can be variously constructed to conform to the particular configuration of the connection site 16. In the illustrated embodiment, where the site 16 is generally tubular in configuration, the shells 26 and 28 are each of a generally conforming semicircular cross section. Preferably, the shells 26 and 28 are formed of a lightweight, generally rigid material, such as plastic.

The housing shells 26 and 28 are joined together by a flexible web 30. The web 30 serves as a hinge. The shells 26 and 28 can thus be moved about the web 30 between an opened position (as shown in FIG. 1), in which the shells 26 and 28 are spaced apart to accommodate their attachment to the connection site 16, and a closed position (as shown in FIG. 3), in which the shells 26 and 28 are brought together to peripherally surround the connection site 16.

As is shown in FIG. 3, the shells 26 and 28 are preferably releasably locked together when in their closed position. The locking mechanism can vary. In the illustrated embodiment, a latch 32 on one of the housing shells 28 locks with a mating tab 34 on the other housing shell 26.

First means 36 situated on an end 38 of the shell 26 secures one end 40 of the connection site 16. In the illustrated embodiment (see FIG. 2), the secured end 40 of the connection site 16 is adjacent to the spike member 12.

Preferably, as is shown in FIGS. 1 and 4, corresponding securement means 37 is situated on the other shell 28. Together, the means 36 and 37 cooperate to securely hold the site end 40 in place when the shells 26 and 28 are in their closed position.

Figure 7:
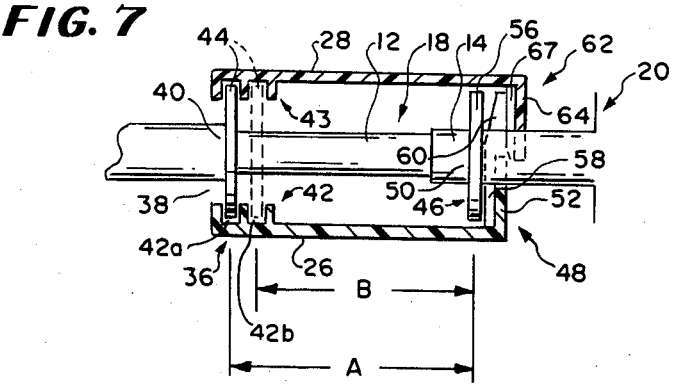
FIG. 7 is a cut-away side view of the interior of the protective shroud taken generally along line 7—7 in FIG. 3.

The securement means 36 and 37 may be variously constructed, depending upon the configuration of the site end 40 and the selection of means to grasp and secure it. In the illustrated embodiment, an annular flange 44 surrounds the spike member 12. The securement means 36 and 37 form at least one groove 42 on the interior of the shells 26 and 28. As shown in FIG. 7, the groove 42 engages the flange 44 associated with the spike member 12. Once the groove 42 and the flange 44 are engaged, movement of the spike end 40 both toward and away from the port end 46 is prevented.

Second means 48 is located on the opposite end 50 of the housing shell 26 to restrain the port end 46 of the connection site 16. In accordance with the invention, the second means 48 includes a wall 52 which is operative, when the spike end 40 of the connection site 16 is secured by the first-described securement means 36, for contacting the port end 46 of the connection site 16. A planar surface in the form of a flange 56 is located on the port end 46 to rest against the wall 52 (see FIG. 7).

The wall 52 restrains the port end 46 of the site 16 against movement away from the spike end 40. This movement, if unchecked by the wall 52, would break the connection with the spike end 40. At the same time, however, the restraining wall 52 does not restrain movement of the port end 46 of the site 16 toward the spike end 40. Movement in this direction preserves the connection site 16 and, as will be described later, can be used to even enhance the integrity of the connection site 16 when placed in association with the shroud 18.

The second means 48 can be variously located within the housing shell 26. In the illustrated embodiment, the wall 52 closes the end 50 of the housing shell 26. The wall 52 includes a cut out portion 54 through which the port 14 is received.

Preferably, the second means 48 includes means for directing the port end 46 into the housing shell 26 to firmly seat the connection site 18 within the shell 26, with one end 40 engaged by a groove 42 and the other end 46 pressed up against the wall 52.

To achieve this, in the illustrated embodiment, the wall 52 includes a pair of upstanding shoulders 58 which extend outwardly from the wall 52 and into the interior of the shell 26 along opposite sides of the cut out portion 54. The shoulders 58 include tapered upper portions 60. As the port end 46 of the site 16 is pressed by the user into the shell 26 (see FIGS. 8 and 9), the port flange 56 slides first along the tapered portions 60 and then along the upstanding regions of the shoulders 58. The flange 56 is thereby led into firm abutting contact against the shoulders 58 and, thus, against the wall 52 itself.

Third means 62 is situated on the mating end of the housing shell 28 to strengthen the restraining wall 52 of the shroud 18. The third means 62 defines a second wall 64 which closes the end 60 of the second shell 28. The wall 64 includes a cut-out portion 65 which aligns with the cut out portion 54 when the shells 26 and 28 are brought together.

As can best be seen in FIG. 4, the wall 64 of the second shell 28 extends slightly beyond the end of the restraining wall 52 of the first shell 26. Thus, when the first and second shells 26 and 28 are brought together into their closed position (see FIGS. 3 and 7), the second wall 64 closely overlaps the first wall 52. In the illustrated embodiment, the second wall 69 overlaps the first wall 52 in the region of the upper tapered portions 60 of the upstanding shoulders 58.

Thus, when the shells 26 and 28 are closed, the second wall 54 buttresses the first wall 52. The wall 52 is thereby reinforced and strengthened to resist yielding in response to forces pulling on the port 14 in a direction which would serve to separate the port 14 from the spike 12.

To enhance the buttressing effect achieved, in the illustrated embodiment, the second wall 64 also includes shoulders 67 which, when the wall 64 overlaps the wall 52, actively press against the exterior of the wall 52.

The shroud 18 is therefore structurally reinforced to provide a secure nest for the connection site 18. The shroud 18 not only protects the connection site 16 from touch contamination, but, due to its reinforced construction, the shroud 18 also significantly strengthens the connection site 16 and prevents the connection members 12 and 14 from being inadvertently separated during use.

Attention is now directed back to FIG. 2. There, it is shown that the overall length of the connection site 16 which is intended to be protected and strengthened by the shroud 18 can vary, depending upon the force with which the spike member 12 is inserted into the port 14. The insertion force, of course, varies with the strength of the user or the mechanical advantage of the connection assist device used. Even the same user and connection assist device do not consistently apply the same insertion forces. Furthermore, the tolerances of the port 14 and spike 12 vary.

As shown in solid lines in FIG. 2, by applying one insertion force, the portions of the site 16 which are engaged by the shroud 18 i.e., flanges 44 and 56, are separated by Distance A.

However, as shown in phantom lines in FIG. 2, if a harder insertion force is applied, the flanges 44 and 56 will be spaced closer together, at Distance B.

In accordance with the invention, the shroud 18 accepts connection sites formed with different insertion forces, thereby having differing overall lengths.

More particularly, the first means 36 includes a series of spaced engagement sites for the end 40 of the connection site. In the illustrated embodiment, the multiple engagement sites comprise multiple, uniformly spaced grooves 42a and 42b, each of which is capable of engaging the flange 44.

As shown in FIG. 7, when the connection site 16 has the overall length A, as the port flange 56 rests against the end wall 52, the spike flange 44 is engaged in the groove 42a. As shown in phantom lines in FIG. 7, when the connection site 16 has the overall length B, as the port flange 56 rests against the end wall 52, the flange 44 is engaged in the groove 42b.

Figure 8:
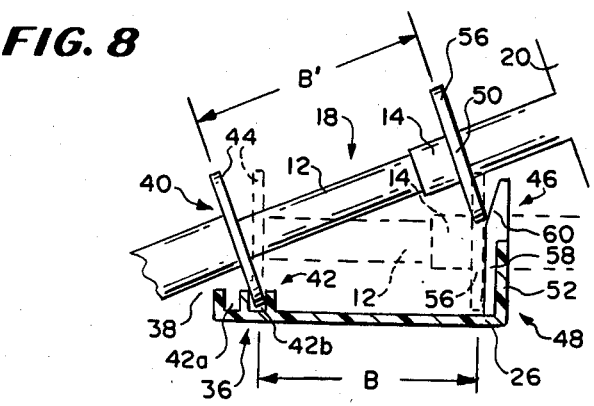
FIG. 8 is a cut-away side view of the interior of one housing shell of the protective shroud as an oversized connection site is being inserted.

In FIG. 8, the site 16 has an overall length B', which lies between overall length A and overall length B. In accordance with the invention, the shroud 18 accepts connection sites of this intermediate length, too.

More particularly, by resting the spike flange 44 in the groove 42b, the port flange 56 can be pivoted against the tapered portions 60 of the end wall shoulders 58 by the application of a downward force (shown by an arrow in FIG. 8). This downward force presses the port end 46 of the connection site 18 into the confines of the housing shell 26. As the port end 46 is pressed into confines of the shell 26, the tapered shoulders 58 compress the port end 46 of the connection site 16 progressively against the secured spike end 40 of the site 16. The initial overall length of B' is thereby reduced into the compressed length B. At this compressed length B, the connection site 16 is securely nested within the shell 26. The shroud 18 will thus protect and strengthen the once-intermediate sized connection 16 in the manner already described.

The particular effect of the compression exerted by the shoulders 58 upon the port end 46 of the connection site 16 will vary according to the material of the flange 56. If the material of the flange 56 is generally rigid, the compression will principally move the port 14 further onto the spike member 12. If the material of the flange 56 is generally flexible, the compression will principally cause deformation of the flange 56 about the spaced-apart shoulders 58. In either case, the effective overall length of the connection site 16 is less in the compressed condition than in its initial condition.

Figure 9:
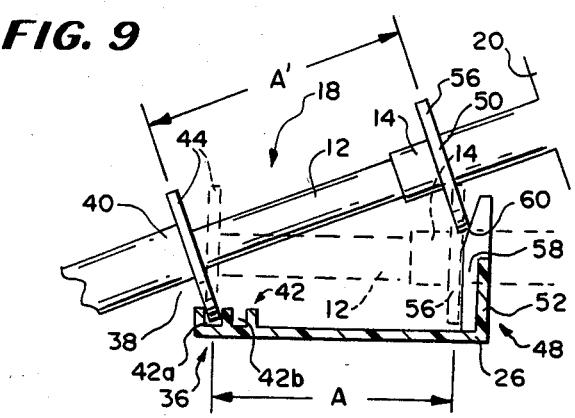
FIG. 9 is a cut-away side view of the interior of one housing shell of the protective shroud as another oversized connection site is inserted.

In FIG. 9, the site 16 has an overall length A' which is greater than overall length A. In accordance with the invention, the shroud 18 accepts connection sites of this oversized length, too.

More particularly, by placing the spike flange 44 into groove 42a and by pressing the port flange 56 against the tapered portion 60 of the shoulders 58 in the manner just described, the initial overall length A' of the connnection site is reduced by compression to length A. At the same time, the port flange 56 is firmly seated against the shoulders 58. Again, at this compressed length A, the connection site 16 is firmly nested within the shell 26. The shroud 18 will protect and strengthen the once-oversized site 16 as heretofore described.

The shoulders 58 therefore provide a positive camming action which, as the site end 46 is pressed into the shell 26, compresses the site 16 to an effective length which securely nests within the shroud 18 and in which the shroud 18 can best protect and strengthen the site 16.

The camming action optimizes the effectiveness of the shroud 18. It assists the user in forming a connection site which, in association with the shroud 18, is most likely to resist accidental separation.

The invention thus provides a highly effective and versatile protective shroud for a connection site. The shroud not only protects the connection site from touch contamination, but it also strengthens the connection site and prevents inadvertent disconnection. The shroud also accepts connection sites of different overall lengths, locating each site 16 into a securely nested relationship within the shroud to withstand the forces which, if unchecked, could pull the connection site apart. In this respect, the shroud operates independent of the ability of the user to form the optimal connection site in the first place.

Various of the features of the invention are set forth in the following claims.

We claim:

1. A protective shroud for a connection site formed between first and second connectors which are slidingly engaged together, the connection site being formed by the user to have an initial length, said protective shroud comprising a body member having an interior area for receiving the connection site, first means on one end of said body member for securing one end of the connection site, second means on the opposite end of said body member defining a restraining wall operative, when the connection site is secured at one end by said first means, for restraining the opposite end of the connection site against movement in a direction which would separate the first and second connectors, the distance between said restraining wall and said first means being less than the initial length of the connection site, and cam means associated with said restraining wall and operative, when the connector site is secured at one end by said first means and a force is applied to the opposite end of the connector site to press the opposite end into the interior area of said body member, for compressing the connection site to reduce its overall length from the initial length to a compressed length which is generally equal to said distance between said restraining wall and said first means and in which compressed length the opposite end of the connection site is seated against said wall and the one end of the connection site secured by said first means.

2. A protective shroud according to claim 1
wherein said body member includes mating first and second housing shells, said first means being located on said first housing shell, and
wherein said second housing shell includes means cooperating with said first means for securing the one end of the connection site when said first and second housing shells are mated together.

3. A protective shroud according to claim 2
wherein said restraining wall is located on said first housing shell, and
wherein said second housing shell includes a wall which overlaps said restraining wall to buttress said restraining wall when said first and second housing shells are mated together.

* * * * *